United States Patent
Shoenfeld

(10) Patent No.: US 8,063,735 B2
(45) Date of Patent: Nov. 22, 2011

(54) REMOTELY ACTUATED REFRIGERATOR LOCK WITH THERMAL SPOILAGE PROTECTION

(75) Inventor: Norman A. Shoenfeld, Livingston, NJ (US)

(73) Assignee: SIS X-Ray Products, Inc., Pen Argyl, PA (US)

( * ) Notice: Subject to any disclaimer, the term of this patent is extended or adjusted under 35 U.S.C. 154(b) by 428 days.

(21) Appl. No.: 12/470,541

(22) Filed: May 22, 2009

(65) Prior Publication Data

US 2009/0231132 A1 Sep. 17, 2009

Related U.S. Application Data

(63) Continuation-in-part of application No. 11/391,986, filed on Mar. 29, 2006, now abandoned.

(51) Int. Cl.
*G08B 21/00* (2006.01)
(52) U.S. Cl. .......... 340/5.73; 340/542; 340/585; 62/129
(58) Field of Classification Search .................. 340/540, 340/542, 584, 585, 588, 5.73; 62/125–131
See application file for complete search history.

(56) References Cited

U.S. PATENT DOCUMENTS

| 6,788,997 | B1 * | 9/2004 | Frederick | 700/236 |
| 2005/0140510 | A1 * | 6/2005 | Elwood et al. | 340/540 |
| 2005/0279122 | A1 * | 12/2005 | Cohen et al. | 62/441 |

* cited by examiner

*Primary Examiner* — Jeffery Hofsass
(74) *Attorney, Agent, or Firm* — Bernhard P. Molldrem, Jr.

(57) ABSTRACT

A remotely actuable refrigerator door lock has a body portion attached to the cabinet and a door portion attached to an edge of the door. A latch in the body portion engages a strike plate in the door portion and can be remotely lifted to open the refrigerator. The door lock assembly is connected to a remote host computer via a USB or ethernet connection. Temperature and/or humidity in the refrigerator is compared with a predetermined limit, and in the event the sensed value is beyond the limit, the remote opening functionality is disabled, and a microprocessor automatically generates and sends a warning message. A key lock can provide access in the event of an adverse temperature or humidity event. The host computer keeps an audit trail of the times and personnel accessing each refrigerator. The system may be used in hospital for controlling access to pharmaceuticals or may be used in a weight loss program.

19 Claims, 4 Drawing Sheets

REMOTELY ACTUATED REFRIGERATOR LOCK WITH THERMAL SPOILAGE PROTECTION

This is a Continuation-in-part of U.S. patent application Ser. No. 11/391,986, filed Mar. 29, 2006 now abandoned. Applicant also claims priority of application Ser. No. 11/653,726, Jan. 16, 2007, and Ser. No. 11/800,937, May 8, 2007. The contents thereof are incorporated by reference herein.

BACKGROUND OF THE INVENTION

This invention relates to an electronically actuated lock that mounts on the front door of a refrigerator to limit access to the refrigerator. The invention is more specifically directed to a refrigerator door lock that connects to a remote computer system, e.g., in a hospital or health care facility, to secure pharmaceuticals that need to be refrigerated, and to facilitate keeping an audit trail of access to the refrigerator. The invention may also be employed as an adjunct to a weight loss program.

In general, pharmaceuticals are delivered to patients when needed, and those that need to be kept refrigerated are stored in a refrigerator in the pharmacy of the hospital or other facility. However, it is more convenient and better use of the nurse's time and efforts to keep the pharmaceuticals at the patient locations, i.e., in the patient's room or ward, or in the cluster of rooms where the patient is located. However, those drugs that need refrigeration cannot simply be stored in a secured dispensing cabinet at the room or nurse station, but have to be kept in a refrigerator until needed. The refrigerator is either unsecured, or is kept locked with a key lock, with the key distribution limited only to certain persons in the nursing staff and pharmacy staff. Any record of access to the refrigerator would have to be maintained on a paper record, or by separately keying in information on separate computer work station. There is also no means provided to ensure that the refrigerator is kept locked, to alarm if the refrigerator is left open or unlocked, or to monitor the refrigerator's operating temperature.

Another object is to provide for notification, by electronic means (e.g., text message or email message), of the pharmacy department when the pre-specified environmental conditions within the refrigerator have not been met.

It would be desirable to employ a refrigerator as a pharmacy cabinet at the patient location in which medications that have been prescribed for a patient can be loaded by pharmacy staff and stored securely until administered to the patient, which will automatically keep track of access to the refrigerated cabinet, and which can be accessed by the nurse staff electronically (e.g., using wireless means). It is also desirable to ensure that the refrigerated cabinet is kept secure, and that the operating temperature is sufficiently cool. However, no measure exists, up to the present, to carry this out.

It is also desirable to integrate the refrigerator lock with the continuous monitoring of the internal temperature (and/or humidity) of the refrigerator, and to take steps to prevent materials from being distributed from the refrigerator if conditions indicate that the contents may potentially be compromised.

A similar problem exists for selectively locking and unlocking a food storage refrigerator at specific meal times in a weight loss or weight control problems.

OBJECTS AND SUMMARY OF THE INVENTION

Accordingly, it is an object of the present invention to provide a remotely actuated refrigerator door locking arrangement that avoids the drawbacks of the prior art.

It is another object to provide a locking refrigerated cabinet and keeps track of the identity or persons accessing the refrigerator and times of such access, for each of a number of refrigerators or refrigerated cabinets throughout a facility that are provided with similar remotely actuated door locks.

It is still another object to provide a refrigerator door lock that senses whether the door is open or closed, signals the remote computer system about the open/closed status of the door, and provides status of the interior temperature of the refrigerator cabinet.

A further object is to provide an audible indication, e.g., with a sounder contained in the door lock enclosure, when the refrigerator door has been kept open longer than a predetermined, programmed time limit.

Another object is to provide the electronic door lock mechanism with a key lock override that can be used, e.g., during a power outage, to obtain access to the medications kept in the refrigerator.

In accordance with an aspect of the present invention, a refrigerator is provided with a remotely opened lock, where the refrigerator is used for storing medications or other substances where access has to be controlled. The lock is opened electronically using a USB or ethernet cable (or similar serial cable device) that is connected to a computer or computer network. The lock may include a temperature detector (and/or a humidity sensor) to monitor whether the temperature (or humidity) level inside the refrigerator cabinet is acceptable for the stored pharmaceuticals or other perishable products. In combination with the lock device, software which may be in the remote computer system, keeps an audit trail of when the refrigerator was opened, and who opened it. The same software and network can control multiple locks on different refrigerators throughout a facility, i.e., nursing home, hospital, or other health care facility. The temperature is automatically monitored and in the case that the temperature drifts outside a predetermined safe range for the contents of the refrigerator, the circuitry within the body of the lock can disable the facility that normally allows remote electronic unlocking of the refrigerator lock.

According to a preferred embodiment, a remotely actuable refrigerator door lock arrangement locks and unlocks a refrigerator cabinet. The lock arrangement has a body portion that mounts onto the body of the refrigerator cabinet and a door portion that mounts onto the door or the refrigerator cabinet aligning with the body portion when the refrigerator door is closed. The door portion has an enclosure that mounts to the door, with a latch strike member, i.e., latch strike plate, situated within the enclosure. The lock body portion likewise has an enclosure that mounts onto the body of the refrigerator cabinet. A latch member projects from the enclosure to engage the latch strike member. A motor drive mechanism, which may include a servo motor, moves said latch member from an engaged or lowered position, in engagement with the latch strike member, to a released or raised position out of engagement with the latch strike member so as to unlock the refrigerator. A USB cable extends from the enclosure of the body portion to connect, either directly or via a network, with a remote computer system. As an alternative to the USB cable, wireless networking (WiFi, Bluetooth, RFID, etc.) can be utilized for PC-to-remote lock communication. An electronics circuit board within the enclosure of the body portion has circuitry for communicating over the USB cable with said remote computer system, and has circuitry, e.g., a microprocessor, that is suitably programmed circuit means for receiving and interpreting commands specific to that specific refrigerator door lock to actuate the motor drive and move the latch member out of engagement with said latch strike member, to provide authorized access to the pharmaceutical refrigerator. The door portion may preferably have a key lock cylinder that is mechanically coupled to the latch strike member, so that the lock can be manually opened, by moving the latch strike member out of engagement with the latch member.

In a preferred arrangement, the latch member has a slant distal surface for moving the latch member over the strike member when the refrigerator door is pushed to its closed position, and also has a recess proximal of that slant surface for engaging said latch strike member so it remains in locked engagement until the latch member is lifted to the release position.

A magnetic (or other equivalent) sensor mechanism within the door lock senses the open/closed state of said refrigerator door. In one embodiment, the sensor mechanism includes a magnet positioned in the enclosure of the door portion and a magnetic sensor portion positioned in the body portion to sense the presence of the magnet when said refrigerator door is closed. The door lock can also incorporate a sounder device that becomes actuated, or sends electronic notification (text message or email message) when the door lock has been sensed to be in its open state longer than a predetermined time limit.

An LED (which may be a two-way Red/Green LED) or other visible indicator is situated in door portion of the lock further comprises a visible indicator showing the open/closed status of the refrigerator door lock.

The remote computer system preferably includes software assigning a respective serial number code to each individual refrigerator door lock permitting said remote computer system to lock and unlock independently each of a plurality of door locks similarly connected with said remote computer system. The software can also include audit trail programming for recording time of opening of each refrigerator door lock connected with said remote computer system and also recording identity of each requesting person associated with such openings of the refrigerator door lock. The key lock permits pharmacy personnel to address a lockout condition that may occur due to temperature or humidity problems.

The pharmacy staff can distribute the various patient prescription orders e.g., during non-busy hours, and deposit the temperature sensitive medications into the patient refrigerator. Then the medications are ready for the nurse or other care giver to administer on schedule, without having to bring a cart from room to room.

Similar refrigerator or temperature controlled cabinets may be used in the radiology laboratory for controlled storage of items such as radiology contrast materials of or other temperature-sensitive pharmaceuticals.

The above and many other objects, features, and advantages of this invention will become apparent from the ensuing description of a selected preferred embodiment, which is to be considered in connection with the accompanying Drawing.

DETAILED DESCRIPTION OF THE PREFERRED EMBODIMENT

A preferred embodiment of this refrigerator lock can be favorably applied in a satellite pharmacy (on the patient hospital floor). In addition, the mechanism can be used to control drug monitoring in any location where temperature sensitive/humidity sensitive pharmaceuticals are stored. Another effective application of this is to follow these environmental parameters in a pharmaceutical distributor's facility. If there is a problem in the evening, the PC and remote lock, powered by an uninterruptible power supply, can send a text message to the facility director to notify him that there is an issue in time to deal with the problem, before the need arises to simply dispose of a large quantity of expensive medications.

Figure 1:
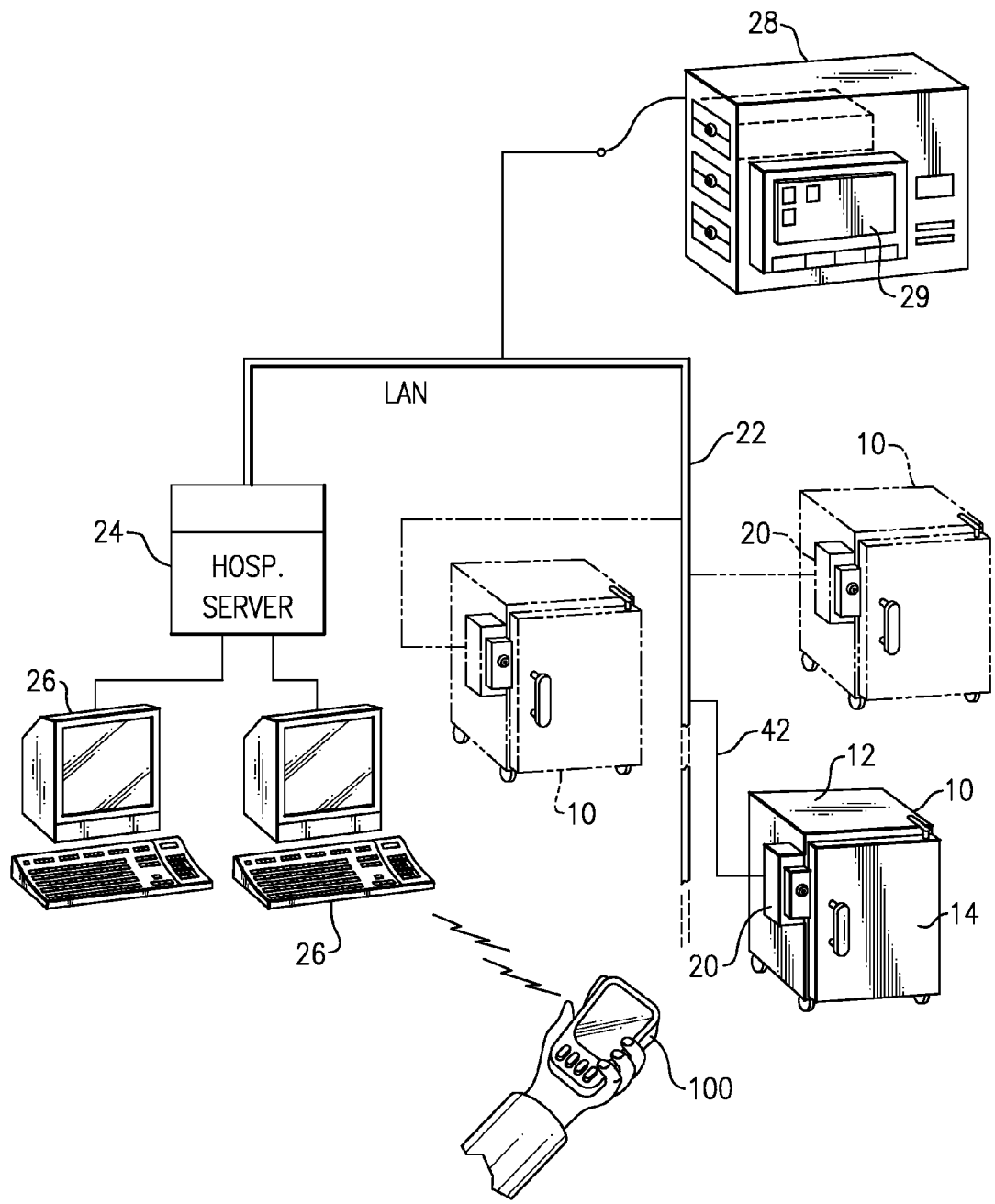
FIG. 1 is a schematic view of a network-connected system including medication storage refrigerator(s) with the door lock arrangement according to one preferred embodiment of this invention.
Figure 2:
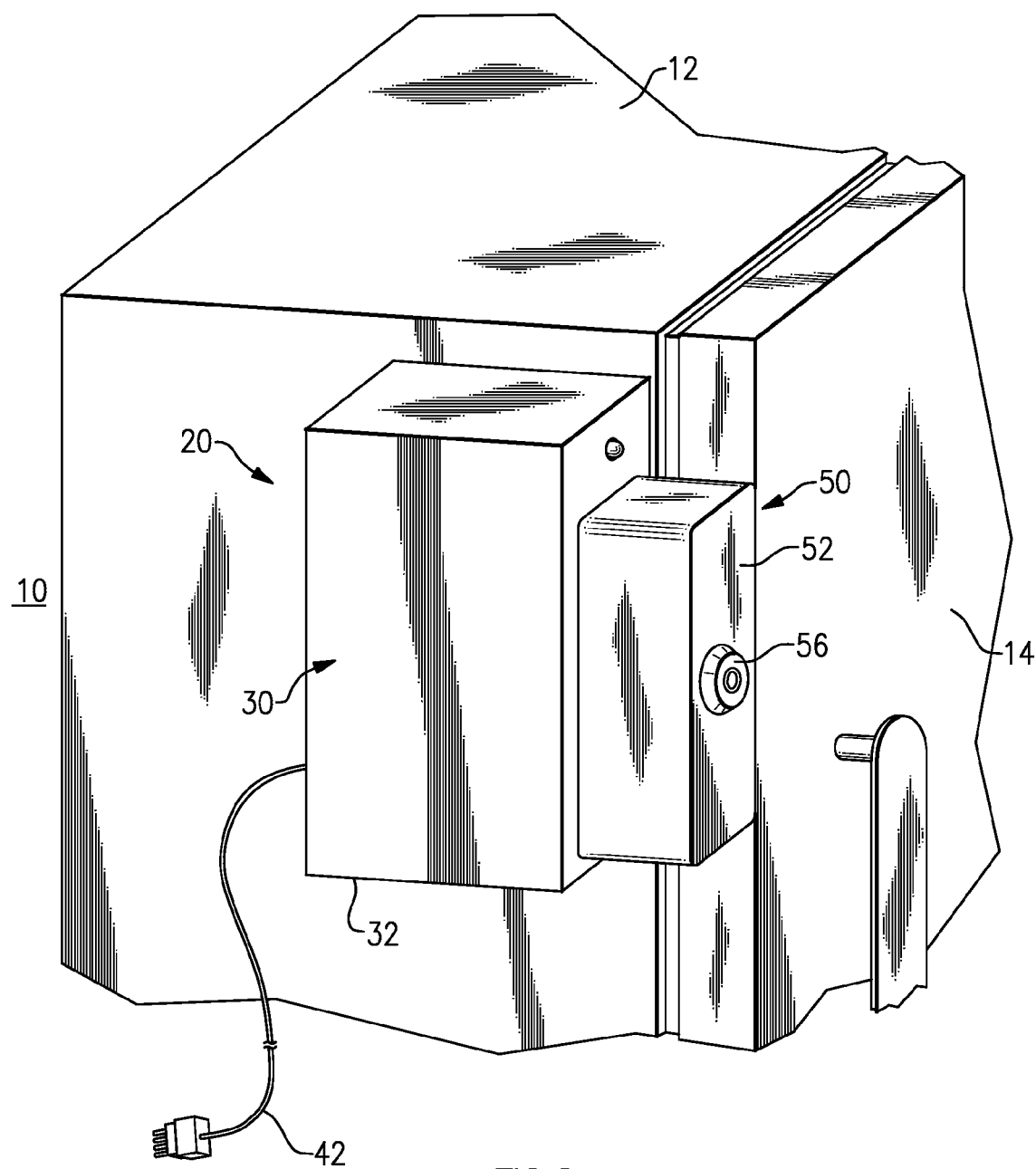
FIG. 2 is a perspective view of the embodiment.

With reference to the Drawing, and initially to FIGS. 1 and 2, a medication dispensing arrangement in a hospital or other health care facility employs one or more small refrigerators 10 in the patient rooms (or at the hubs of clusters of patient rooms) for storage and controlled access to medications and pharmaceuticals that need to be kept refrigerated. The refrigerator 10 has a cabinet body 12 and a door 14 that closes over the front of the cabinet body. In the illustrated embodiment, the door 14 is hinged at the right and opens from the left, but the refrigerator could as easily be a right-opening version. Typically, the door and cabinet have a magnetic closure of sufficient strength to maintain compression on the door seal. In this embodiment, the refrigerator has attached onto it a remote actuation door lock assembly 20, as described in more detail later. The door lock assembly is connected electrically or electronically via a network 22, e.g., a LAN, that makes either a wired or wireless connection with a hospital computer server 24, to which one or more work station computers 26, 26 are connected. The LAN 22 can also connect with door lock assemblies 20 for additional med storage refrigerators 10, here shown in broken line. These may be located in other patient rooms or in other locations throughout the facility.

Also shown here is a wall mounted medications cabinet 28, which may be mounted on the wall of the patient room in which the refrigerator 10 is located, and which is also coupled electronically with the hospital LAN 22. The purpose of the wall mounted cabinet 28 is to provide controlled access in the patient's room to non-refrigerated medications in one or more computer locked drawers. In this version, the cabinet 28 has an associated touch-screen computer 29 on which the nurse or other authorized health care provider can enter an authorization code to achieve access to the cabinet drawer(s). The same touch screen computer 29 may be used via the LAN 22 to release the lock mechanism on the refrigerator lock 20. Alternatively, the health care provider may employ a wireless hand-held device 100 that communicates with one of the computer work stations 26 to unlock the refrigerator lock 20.

In an alternative embodiment, e.g., in a physician's office, the refrigerator may be free standing, with its lock 12 coupled to a local computer or to a small LCD device with a programmed microprocessor, which may be mounted on the refrigerator, for entering an unlock code to open the refrigerator, and which will keep an audit trail of times of opening and closing.

As shown in more detail in FIG. 2, the refrigerator door lock assembly 20 has two main components, namely, a body portion 30, with an enclosure or housing 32 that is affixed onto a side wall of the refrigerator cabinet body 12, and a door portion which has an enclosure or housing 52 that is affixed to an edge of the door 14, and which is aligned with the body portion 30. The body portion 30 and door portion 50 are shown here mounted on the left side wall of the cabinet body and left edge of the door, but the housing is adapted to be mounted on either the left or right side, depending on the side on which the refrigerator door opens.

An indicator LED 33 is shown here on the front wall of the body portion 30, to show the locked/unlocked status, and a USB cable 42 or ethernet cable extends from the body portion for attaching to the LAN 22 or otherwise to the remote computer, i.e., the hospital server 24. A key lock 56 is provided on the door portion 50 to permit the refrigerator lock to be unlocked manually, e.g., in the event of a power failure or computer system failure or outage, or in case of a lockout due to temperature or humidity problems.

Figure 3:
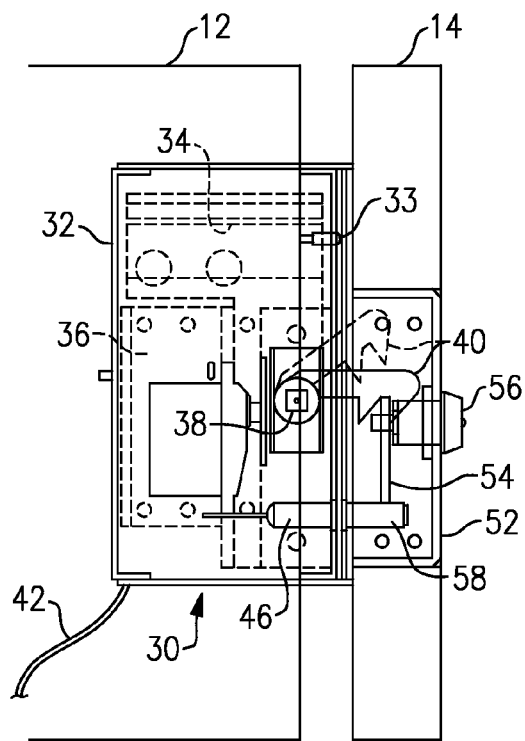
FIG. 3 is a side view of this embodiment
Figure 4:
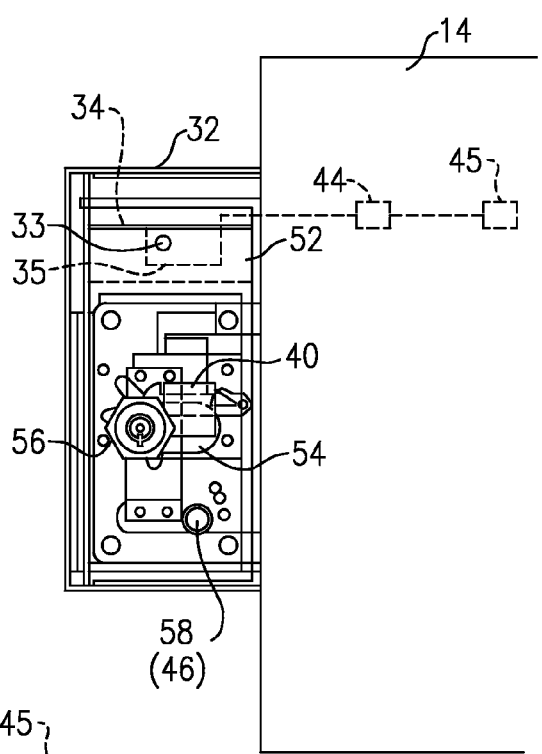
FIG. 4 is front view of this embodiment.
Figure 5:
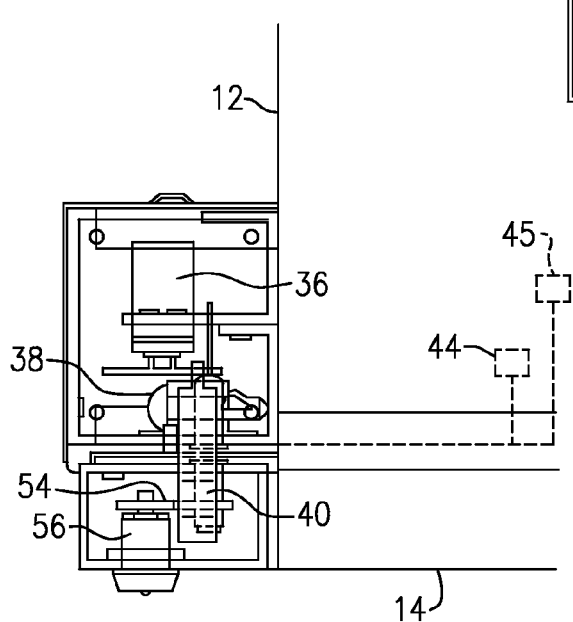
FIG. 5 is a top view of this embodiment.

The interior arrangements of the body portion 30 and door portion 50 of the refrigerator lock assembly are shown in more detail in FIGS. 3, 4, and 5.

Within the housing 32, the body portion 30 contains an electronics circuit board 34, which includes an ethernet port or USB port and suitably programmed controller microprocessor, which can be programmed to accept and/or transmit self-descriptive command data packets, so that the hospital computer system will assign each refrigerator lock assembly a unique identifier code. As is well known in the art, an interpretive communicative software driver within the hospital server 24 or other host computer contains and/or uses a library of pre-defined peripheral USB drivers to control the USB-based door lock assemblies. A customized USB driver engineered specifically for this refrigerator lock can also be uploaded onto the hospital server. A similar system is employed when ethernet or other network system is employed. The host computer assigns a unique code or serial number for each individual refrigerator door lock assembly 20. This permits the computer system to lock and unlock each of a large number of refrigerator door locks independently or one another.

A microprocessor that is included on the circuit board 34 is programmed to open the refrigerator lock remotely when an unlock code is received. The microprocessor also is programmed with a predetermined temperature limit, i.e., a high temperature limit, a low temperature limit, or both, which can be set by pharmacy personnel. A humidity limit can also be set and programmed into the microprocessor. In the event that there is a temperature event (or humidity event) detected, i.e., the temperature in the interior of the refrigerator cabinet is outside the temperature limit (or alternatively the temperature remains outside the limit for some period of time), the microprocessor will automatically block the facility for remote opening of the lock. The microprocessor also includes a facility for generating an alert message if a temperature event of that type occurs (or if the detected humidity is too high or too low). The alert message will identify the refrigerator and the nature of the problem, and will automatically be transmitted (as an email or text message) to a predetermined addressee (or addressees), and sent over the hospital computer network.

The circuit board 34 carries out the remote opening feature by providing drive power to a servo motor and drive 36 for unlocking or releasing the door portion 50. In this embodiment, there is a transverse pivot pin 38 on which a latch lever 40 is pivoted for motion between a lower latched position (shown in solid) and a raised unlatched position (shown in ghost or broken line). The latch lever 40 has a slanting nose surface at its distal end, and a recess behind this for securing a latch strike plate 54 in the door portion 50. The slanting nose surface allows the lever to lift and then drops to latch and capture the strike plate when the refrigerator door closes.

The USB or ethernet cable 42 plugs into a suitable socket or jack on the circuit board 34. A serial-ethernet bridge interface may be used here. The host computer, e.g. hospital server 24, may use a Window, UNIX, LINUX or other suitable system. The system can employ a card reader, e.g., bar code or magnetic stipe, RFID, or smart-card reader to provide access and unlock the lock assembly 20, in which case access may be by means of a card or badge carried by the health care provider. A suitable reader device could be installed within the medications cabinet 28 in the same room as the refrigerator.

The power for the latch motor servo can be provided from the USB port, or suitable DC can be obtained from the LAN to power the motor 36 (and also power the LED indicator 33 and sounder 35). Alternatively, an internal battery may be used in the body portion enclosure 32, or power can be derived from the associated refrigerator 10. An external DC power supply may also be used.

Also shown here are a temperature sensor 44 and a relative humidity sensor 45 that are positioned in the interior of the cabinet body 12 and connect by wire to the circuit board 34. A magnetic proximity sensor 46 is disposed at a front surface of the body portion 30, and is coupled to the circuit board 34 to provide an indication of the open/closed status of the door 14, which can then be communicated via the cable 42 and LAN 22 to the hospital computer system. The system can be programmed to alert the pharmacy personnel if one of the refrigerators fails to maintain a sufficiently cool interior temperature. This may be done by transmission of a text message or electronic mail automatically generated by the microprocessor of the circuit board 34.

The LED lock/unlock status indicator 33 in this embodiment is adapted to glow red when the lock assembly 20 is locked, and to glow green when the lock assembly is unlocked. A no-glow or dark indication then indicates a fault or possible system failure. Flashing on-off intermittently can indicate, e.g., a temperature problem, i.e., that the temperature sensor 44 has detected a high temperature condition. A flashing signal at a different rate can be used to indicate that the relative humidity is too high or too low, as sensed by the humidity sensor 45.

An audible sounder 35 within the body portion housing 32 emits a tone or buzz if the refrigerator door remains open for a time that exceeds a predetermined time limit. The time limit can be programmed, e.g., from one of the work stations 26. The sounder alerts the nurse or other authorized attendant to close the refrigerator door, if the door has been inadvertently left open.

The distal end of the latch lever 40 protrudes out beyond the front wall of the body portion enclosure 32, and there is also an access opening at the rear wall of the door portion enclosure 52 to permit entry of the latch lever 40 so it can engage the strike plate 54. In this embodiment, the latch strike plate 54 is mounted on the key lock cylinder 56, so that the latch strike plate 54 can be rotated down and out of engagement with the latch lever, if necessary. This arrangement permits authorized personnel to open the refrigerator manually (with a key) in the event a power failure, network outage, or other event that might preclude obtaining electronic access.

Finally, a magnetic member 58 is situated in the door portion 50 and this is aligned with the magnetic proximity sensor 46 to close the sensor 46 when the door is closed. The proximity sensor 46 remains in its open state when the door is open and the magnetic member is not in proximity.

Other arrangements employing the same general principles can be used in other environments where there is a need to control access to the contents of the refrigerator. One possibility is in connection with a weight control program where access to food is limited to meal times so as to prevent or discourage snacking. Another possibility is in a hospitality environment, where access to reserve supply refrigerators in hospitality suites are to be limited to authorized hotel staff or catering personnel.

In a preferred embodiment, the hospital computer system keeps track of the times each refrigerator is unlocked, and the of identities of authorized personnel who obtain (or attempt to obtain) access, i.e., the system creates an audit trail of health providers who request access.

Figure 6:
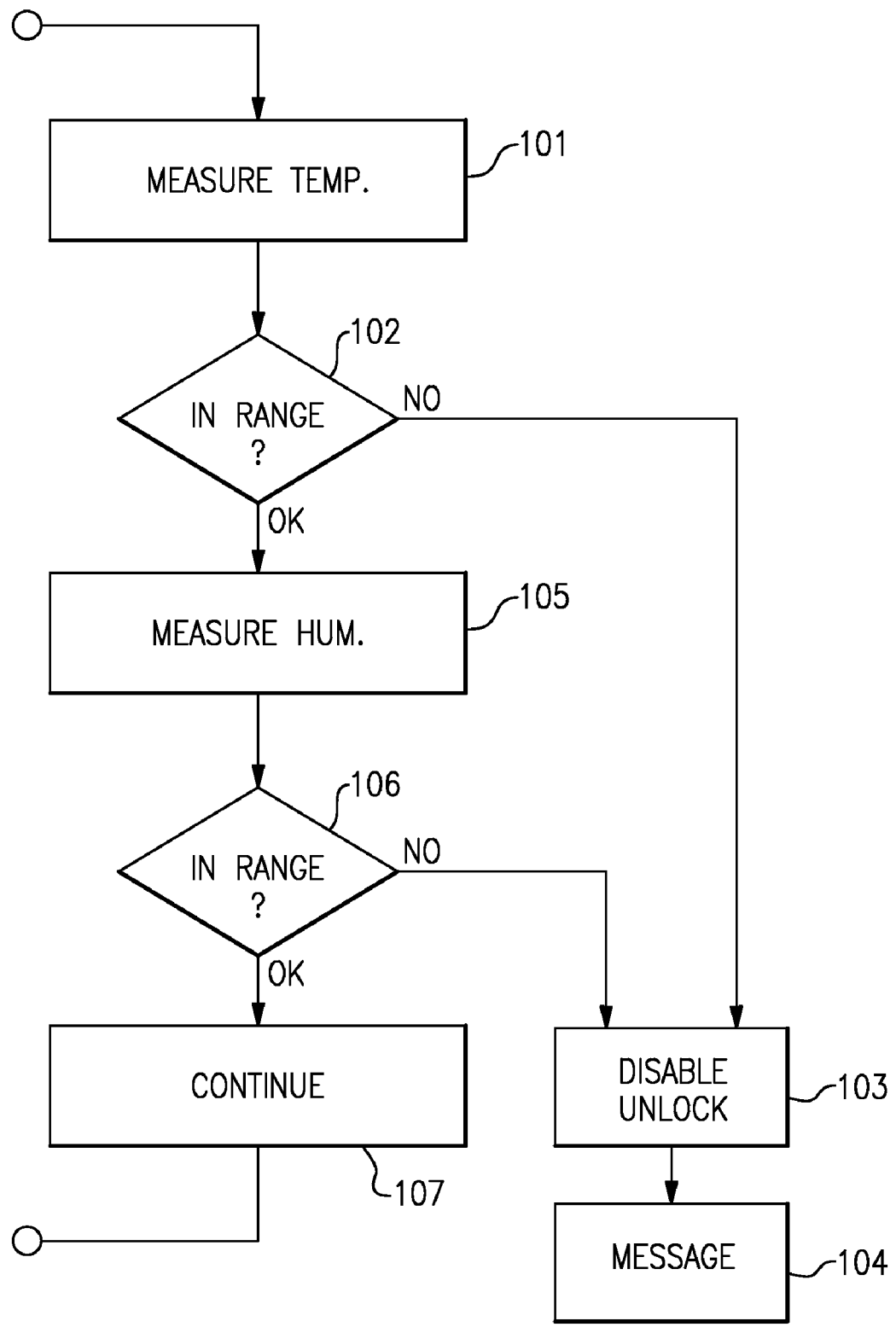
FIG. 6 is a flow chart diagram for explaining a feature of the invention.

With reference to the flow chart of FIG. 6, the existence of an adverse temperature condition inside the refrigerator, i.e., the temperature as received from sensor 44 being outside some predetermined critical range (too low or too high), can trigger the microprocessor to automatically disable the electronic unlock feature, so that persons such as the nurses or care givers will be denied access when the materials, i.e. temperature-sensitive pharmaceuticals, may have been compromised. The unlock feature can optionally be disabled also in the event of an adverse humidity condition, as well. Here, a predetermined temperature limit, which can be a high temperature limit, a low temperature limit, or both, is programmed into the microprocessor on board the circuit board 34. This programming can be carried out remotely or with a hand-held device at the time of loading the refrigerator. The output of the temperature sensor 44 is fed to the microprocessor and is periodically monitored. The output of the humidity sensor 45 is also monitored.

As shown in FIG. 6, the programmed microprocessor measures the temperature (step 101), as detected by the sensor 44, and compares this temperature with the high and/or low temperature limit(s) (step 102). If the temperature is within the acceptable range, then the program will go on to test the humidity level, but if not, this will disable the electronic unlock functionality (step 103), and prevent the microprocessor from energizing the servo motor 36 so the refrigerator lock remains latched closed. The microprocessor then automatically generates a text message or electronic mail message (step 104) that is addressed to an appropriate predetermined addressee, such as the hospital pharmacy. The message identifies the station at which the refrigerator is located, and indicates the nature of the problem.

Where the temperature remains in the proper range, the system goes on to measure the relative humidity (step 105) and compares the measured humidity level with a preset humidity limit or limits (step 106). If the humidity is in the acceptable range, the process continues (step 107) and repeats. If not, the unlock feature is disabled (step 103) and an alert message is sent (step 104). The message can be transmitted electronically (i.e., via cable 42) through the hospital network. The message may also be sent wirelessly, e.g., Blue tooth, to a transmission network.

Once a temperature condition (or humidity condition) occurs such that the refrigerator contents are potentially compromised, the nurse or other patient care giver will be unable to open the refrigerator and access the possibly-compromised materials. This means that the potentially compromised drugs will not be distributed. However, pharmacy personnel (who have been alerted to this situation by electronic message) can access the refrigerator lock by key, and can retrieve the contaminated or potentially compromised drugs. The pharmacy personnel can then replace those drugs with fresh ones, and reset the refrigerator lock to open normally.

While the invention has been described hereinabove with reference to selected preferred embodiments, it should be recognized that the invention is not limited to those precise embodiments. Rather, many modification and variations would present themselves to persons skilled in the art without departing from the scope and spirit of this invention, as defined in the appended claims.

What is claimed is:

1. Remotely actuable refrigerator door lock for locking and unlocking a refrigerator which has a cabinet with a body and a door that closes against said body, with a body portion that mounts onto the body of the refrigerator cabinet and a door portion that mounts onto the door of the refrigerator cabinet to align with the body portion when the refrigerator door is closed;
   the door portion comprising
      an enclosure that mounts to the door; and
      a latch strike member within said enclosure;
   the body portion comprising
      an enclosure mounting to the body of the refrigerator cabinet;
      a latch member projecting from the enclosure to engage said latch strike member;
      a motor drive mechanism for selectively moving said latch member from engagement with said latch strike member to unlock the refrigerator;
      a data communications channel extending from the enclosure of the body portion for connecting with an external computer arrangement; and
   suitably programmed circuit means contained within the enclosure of the body portion for communicating over said data communications channel with said computer arrangement for receiving unlock commands specific to the refrigerator door lock, and the circuit means having a unlock facility to actuate said motor drive to move the latch member out of engagement with said latch strike member upon receipt of said unlock commands specific to said refrigerator door lock;
      a temperature monitor having a probe sensing temperature inside said refrigerator cabinet, the temperature monitor being coupled with said suitably programmed circuit means to transmit the sensed temperature thereto; and
   wherein said suitably programmed circuit means is operative to store at least one predetermined temperature limit, and to compare the sensed temperature with said at least one predetermined temperature limit, and is operative to disable said unlock facility if the sensed temperature is beyond said predetermined temperature limit so that the refrigerator door lock is prevented from being unlocked remotely.

2. Remotely actuable refrigerator door lock of claim 1 wherein said suitably programmed circuit means is adapted to generate and transmit an alert message to a predetermined addressee in the event that said sensed temperature is beyond said predetermined temperature limit.

3. Remotely actuable refrigerator door lock of claim 1 in which said door portion further includes a key lock cylinder mechanically coupled to said latch strike member for moving said latch strike member out of engagement with said latch member.

4. Remotely actuable refrigerator door lock of claim 1 wherein said latch member has a slant distal surface for moving said latch member over said latch strike member when the refrigerator door is pushed to its closed position, and a recess proximal of said slant surface for engaging said latch strike member.

5. Remotely actuable refrigerator door lock of claim 1 further comprising sensor means within said door lock for sensing an open/closed state of said refrigerator door, and transmitting an open/closed signal to said suitably programmed circuit means, said sensor means including a magnet positioned in the enclosure of said door portion and a sensor positioned in said body portion to sense the presence of said magnet when said refrigerator door is closed; said sensor being operatively coupled to said suitably programmed circuit means; and said door portion further comprising a visible indicator controlled by said suitably programmed circuit means for showing the open/closed status of the refrigerator door lock.

6. Remotely actuable refrigerator door lock of claim 1 wherein said computer arrangement includes software assigning a respective serial number code to each individual refrigerator door lock permitting said computer arrangement to lock and unlock independently each of a plurality of door locks similarly connected with said remote computer system.

7. Remote actuable refrigerator door lock of claim 6 wherein said software includes audit trail means for recording time of opening of each refrigerator door lock connected with said remote computer system and also recording identity of each requesting person associated with such openings of the refrigerator door lock.

8. Remotely actuable refrigerator door lock of claim 5 further comprising a sounder device on said body portion and coupled to said suitably programmed circuit means, the sounder device being actuated when said door lock has been sensed to be in its open state longer than a predetermined time limit.

9. Remotely actuable refrigerator door lock of claim 1 further including means for communicating a temperature alarm to said remote computer system when the sensed temperature is beyond said limit.

10. Remotely actuable refrigerator door lock of claim 1, comprising a visible indicator controlled by said suitably programmed circuit means which flashes to indicate said temperature being beyond said predetermined limit.

11. Remotely actuable refrigerator door lock of claim 1 wherein suitably programmed circuit means includes a USB interface.

12. Remotely actuable refrigerator door lock of claim 1 wherein said suitably programmed circuit means includes an ethernet interface.

13. A refrigerator door lock for locking and unlocking a refrigerator which has a cabinet with a body and a door that closes against said body, with a body portion that mounts onto the body of the refrigerator cabinet and a door portion that mounts onto the door of the refrigerator cabinet to align with the body portion when the refrigerator door is closed; and comprising a control and display arrangement located external to said body portion;
the door portion comprising
an enclosure that mounts to the door; and
a latch strike member within said enclosure;
the body portion comprising
an enclosure mounting to the body of the refrigerator cabinet;
a latch member projecting from the enclosure to engage said latch strike member;
a motor drive mechanism for selectively moving said latch member from engagement with said latch strike member to unlock the refrigerator;
means connecting with said external control and display arrangement;
suitably programmed circuit means within the enclosure of the body portion for communicating with said control and display arrangement for receiving commands specific to the refrigerator door lock to actuate said motor drive to move the latch member out of engagement with said latch strike member;
a temperature monitor having a probe sensing temperature inside said refrigerator cabinet, the temperature monitor being coupled with said suitably programmed circuit means; and
wherein said suitably programmed circuit means is operative to store at least one predetermined temperature limit, and to compare the sensed temperature from said probe with said at least one predetermined temperature limit, and is operative to disable said unlock facility if the sensed temperature is beyond said predetermined temperature limit so that the refrigerator door lock is prevented from being unlocked remotely.

14. Refrigerator door lock of claim 13, wherein said suitably programmed circuit means is adapted to generate and transmit an alert message to a predetermined addressee in the event that said sensed temperature is beyond said predetermined temperature limit.

15. Refrigerator door lock of claim 13 further comprising magnetic sensor means within said door lock for sensing an open/closed state of said refrigerator door; and communicating with said suitably programmed circuit means, and said suitably programmed circuit means being operative to actuate visible indicator mounted on the enclosure of said body portion, for showing the open/closed status of the refrigerator door.

16. Refrigerator door lock of claim 13 wherein said control and display arrangement includes software for identifying individuals having access to open the refrigerator; and said software further includes audit trail means for recording time of opening of the refrigerator door lock and also recording the identity of each person accessing the refrigerator for each such opening of the refrigerator door lock.

17. Refrigerator door lock of claim 13 wherein said suitably programmed circuit means is coupled to said control and display arrangement for communicating an alarm signal to said control and display arrangement when the sensed temperature is beyond said at least one limit.

18. Refrigerator door lock of claim 17 further including a visible indicator providing a flashing indication when said temperature is beyond said limit.

19. Refrigerator door lock of claim 13 further comprising a humidity sensor positioned within said refrigerator cabinet and being coupled with said suitably programmed circuit means to transmit a sensed humidity thereto; and wherein the suitably programmed circuit means is operative to store at least one predetermined humidity limit, and to compare the sensed humidity from said humidity sensor with said at least one predetermined humidity limit, and is operative to disable said unlock facility if the sensed humidity is beyond said predetermined humidity limit so that the refrigerator door lock is prevented from being unlocked remotely.

* * * * *